(12) United States Patent
Kravchenko et al.

(10) Patent No.: US 10,245,272 B2
(45) Date of Patent: Apr. 2, 2019

(54) TRANSMEMBRANE PENETRATION ENHANCER

(76) Inventors: Iryna Kravchenko, Santa Clara, CA (US); Sergiy Lozovsky, Santa Clara, CA (US)

(*) Notice: Subject to any disclaimer, the term of this patent is extended or adjusted under 35 U.S.C. 154(b) by 53 days.

(21) Appl. No.: 12/911,593

(22) Filed: Oct. 25, 2010

(65) Prior Publication Data

US 2012/0101088 A1 Apr. 26, 2012

(51) Int. Cl.
*A61K 31/5513* (2006.01)
*A61K 47/28* (2006.01)

(52) U.S. Cl.
CPC .......... *A61K 31/5513* (2013.01); *A61K 47/28* (2013.01)

(58) Field of Classification Search
None
See application file for complete search history.

(56) References Cited

U.S. PATENT DOCUMENTS 4,999,348 A * 3/1991 Cioca et al. ............... 514/171
6,413,547 B1 * 7/2002 Bennett et al. ............ 424/489

OTHER PUBLICATIONS

Lin et al. in Journal of Controlled Release 73 (2001) 293-301.*
'Product MSDS Cholesteryl Pelargonate' in www.chemicalbook.com/Product MSMSDetailCB9284098_EN.htm.*
Kravchenko et al. in Pharmaceutical Chemistry 43(1), Jan. 3-10, 2009.*
Drug Definition in http://www.merriam-webster.com/dictionary/drug.*
Rosevear FB. Liquid Crystals: The Mesomorphic Phases of Surfactant Compositions. J. Soc. Cosmetic Chemists, 1968: 19; 581-594.*
Lin et al (J Controlled Release 73:293-302, 2001) (Year: 2001).*

* cited by examiner

Primary Examiner — Craig D Ricci

(57) ABSTRACT

A transmembrane penetration enhancer includes a thermotropic liquid crystal suitably prepared for use in a therapeutic system to improve delivery of at least one active ingredient across a biomembrane and/or skin. The thermotropic liquid crystal comprises at least one cholesteryl ester and is effective in a mesomorphic state at a temperature of the biomembrane and/or skin. A therapeutic system includes the prepared thermotropic liquid crystal for enhanced transmembrane penetration and at least one active ingredient for delivery by the thermotropic liquid crystal. A method for making and using the transmembrane penetration enhancer is presented.

4 Claims, 2 Drawing Sheets

TRANSMEMBRANE PENETRATION ENHANCER

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates to a transmembrane and transdermal penetration enhancer. More particularly, the present invention is a transmembrane and transdermal penetration enhancer by which various active ingredients are transmembrane and transdermally delivered.

BACKGROUND OF THE INVENTION

Transmembrane delivery of different drugs includes transdermal, rectal, intranasal and intravaginal delivery. All these routes have mucous membranes which are a biological barrier in the delivery of exogenous drugs.

Transdermal administration is relatively easy and convenient as compared with oral administration and administration by injection and may also be advantageous in terms of duration of the effect and reduction of expression of the side effects, which also make transdermal administration an excellent administration method. However, in order to permeate the active ingredient into the body by transdermal administration, the active ingredient is to be penetrated through the skin which constitutes a primary barrier of the living body and its bioavailability (the amount of the drug absorbed within a blood flow) is inherently relatively low. Penetration enhancers are therefore needed to boost penetration of a biological membrane for delivery of injected substances utilizing transdermal administration.

To achieve bioavailability of active ingredients being transdermally administered, it has been shown that 1.2-propylene glycol, dipropylene glycol, hexylene glycol, isoparaffin, sodium laurylsulfate, ethylene oxide adducts of lauryl alcohol, fatty acids, ethyl alcohol, polyethylene glycol fatty acid esters, glycerol, polyoxyethylene sorbitan fatty acid esters, propyl carbonate, sodium pyrrolidonecarboxylate, urea, lactic acid, sodium lactate, lecithin, dimethyl sulfoxide, pyrrolidonecarboxylate, nicotinate, N-methylproline ester, amine oxide and other ingredients are prepared for external application as a transdermal absorption enhancer. Most existing transdermal enhancers are synthetic compounds that are considered foreign by a person's body and are not received relatively well.

In view of the foregoing, there is a need for a transmembrane penetration enhancer that is not considered foreign by a person's body and is received relatively well.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
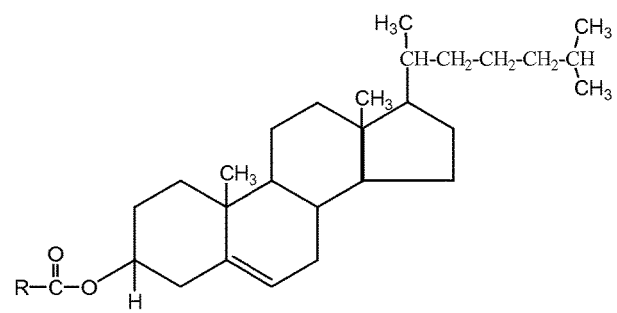
FIG. 1 illustrates an exemplary formulation in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, a transmembrane penetration enhancer is presented.

In one embodiment a transmembrane penetration enhancer includes a thermotropic liquid crystal suitably prepared for use in a therapeutic system to improve delivery of at least one active ingredient through a biomembrane and/or skin. In another embodiment the thermotropic liquid crystal comprises at least one cholesteryl ester. In yet another embodiment the thermotropic liquid crystal exhibits a mesomorphic state at a temperature of the biomembrane and/or skin. Various other embodiments further include cholesteryl succinate, cholesteryl nanilsuccinate, or cholesteryl adipinate. By way of example, in still other embodiments the thermotropic liquid crystal comprises a mixture of cholesteryl pelargonate and cholesteryl valerate are combined with a third ingredient selected from the following: cholesteryl succinate, cholesteryl nanilsuccinate, or cholesteryl adipinate. Other embodiments comprise the following triple combinations: cholesteryl pelargonate, cholesteryl valerate and cholesteryl succinate; cholesteryl pelargonate, cholesteryl valerate and cholesteryl nanilsuccinate; or cholesteryl pelargonate, cholesteryl valerate and cholesteryl adipinate;

In yet other embodiments the thermotropic liquid crystal comprises a mixture of cholesteryl pelargonate and cholesteryl propionate. In still other embodiments the thermotropic liquid crystal comprises a mixture of n-oxybenzal-n-butylaniline and n-metoxybenzal-n-butylaniline. In another embodiment the thermotropic liquid crystal comprises 4-cyano-4-amyldiphenyl. In yet another embodiment the enhancer is operable to improve transdermal penetration. In still another embodiment the enhancer is operable to improve transmucosal penetration.

In another embodiment a therapeutic system includes a thermotropic liquid crystal prepared for improving transmembrane penetration, and at least one active ingredient for improved delivery by the thermotropic liquid crystal. In another embodiment the at least one active ingredient comprises a drug. In yet another embodiment the thermotropic liquid crystal comprises at least one cholesteryl ester. In still another embodiment the thermotropic liquid crystal comprises a mixture of cholesteryl esters selected from a group consisting of cholesteryl pelargonate, cholesteryl valerate, cholesteryl succinate, cholesteryl adipinate, cholesteryl nanilsuccinate and cholesteryl propionate. In another embodiment the thermotropic liquid crystal is operable to improve transdermal penetration. In yet another embodiment the thermotropic liquid crystal is operable to improve transmucosal penetration. In still another embodiment the thermotropic liquid crystal exhibits a mesomorphic state at a temperature of a biomembrane it is applied to.

In another embodiment a method includes steps for selecting cholesteryl esters, steps for combining the cholesteryl esters, steps for fusing the combination, and steps for mixing the fused combination to form a thermotropic liquid crystal operable for improved penetration of biomembranes.

In another embodiment a method includes the steps of selecting one or more cholesteryl esters, combining the one or more cholesteryl esters, fusing the combination, and mixing the fused combination wherein the mixed combination forms a thermotropic liquid crystal operable for improved penetration of biomembranes and skin. Another embodiment further includes the step of adding an active ingredient for improved delivery by the thermotropic liquid crystal. In yet another embodiment the one or more cholesteryl esters is selected from a group consisting of cholesteryl pelargonate, cholesteryl valerate, cholesteryl succinate, cholesteryl adipinate, cholesteryl nanilsuccinate and cholesteryl propionate. In still another embodiment the active ingredient comprises a drug. In another embodiment the thermotropic liquid crystal is operable to improve transdermal penetration. In yet another embodiment the thermotropic liquid crystal is operable to improve transmucosal penetration. In another embodiment the thermotropic liquid crystal exhibits a mesomorphic state at a temperature of the biomembrane and/or skin.

In another embodiment a method includes steps for selecting a thermotropic liquid crystal and an active ingredient for delivery through a biomembrane, and steps for applying the thermotropic liquid crystal to the biomembrane to penetrate the biomembrane and deliver the active ingredient.

In another embodiment a method includes the steps of selecting a thermotropic liquid crystal comprising one or more cholesteryl esters and an active ingredient for improved delivery through a biomembrane, and applying the thermotropic liquid crystal to the biomembrane where the thermotropic liquid crystal enhances the penetration of the biomembrane and the active ingredient is delivered. In another embodiment the one or more cholesteryl esters is selected from a group consisting of cholesteryl pelargonate, cholesteryl valerate, cholesteryl succinate, cholesteryl adipinate, cholesteryl nanilsuccinate and cholesteryl propionate. In yet another embodiment the active ingredient comprises a drug. In still another embodiment the thermotropic liquid crystal is operable to improve transdermal penetration. In another embodiment the thermotropic liquid crystal is operable to improve transmucosal penetration. In yet another embodiment the thermotropic liquid crystal exhibits a mesomorphic state at a temperature of the biomembrane.

Other features, advantages, and objects of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed, but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Some preferred embodiments of the invention provide means and methods for providing a transmembrane and transdermal penetration enhancer by which various active ingredients are transmembrane and transdermally delivered. Cholesterol and its esters are involved with transmembrane and transdermal penetration enhancers when the transmembrane and transdermal penetration enhancers are administered. Cholesterol and its esters are important constituents of cellular membranes and play a fundamental role in many biological processes. Cholesterol affects membrane permeability, lateral lipid organization, signal transduction and membrane trafficking. Relatively large amounts of cholesterol are typically present in the membrane of myelin filament, erythrocytes, hepatocytes and skin.

Cholesterol is the only major sterol of the stratum corneum. Cholesterol is an essential component of the lipid membranes of the stratum corneum and contributes to the lipid layer's stability, fluidity and promotes the liquid condensed state in lipid mixtures, containing unsaturated and saturated diacyl chains. Lipid composition includes ceramides, cholesterol, cholesterylsulphate and free fatty acids.

Cholesterol and cholesteryl esters have many functions. The penetrability of a biomembrane can be changed by application of cholesteryl esters. The inclusion of cholesteryl esters to lipid layers destabilizes them. Cholesteryl esters and fatty acids, as opposed to phospholipids and ceramides can penetrate into the lipid matrix relatively fast. Cholesteryl esters are also hydrolyzed to cholesterol and free fatty acids in the skin. Cholesteryl esters and free fatty acids induce changes at the fluidity, packing density and temperature of phase transition. Influence of cholesterol on the structure and function of the stratum corneum depends on many factors. Inclusion of cholesterol to membranes stimulates an increase of density and a decrease of fluidity. Molecules of cholesterol have vertical position in the plane of lipid layers and their hydroxyl groups are orientated to the water side of the molecule and the hydrocarbon components orientated to the lipid layers. Cholesterol also induces the transition from a lamellar phase to a gel phase and decreases the amount of fixed water in the stratum corneum in vivo.

When the cholesterol is delivered to the stratum corneum by a transdermal delivery system, it activates cholesterol-sulphatase and transforms the cholesterol into cholesteryl sulphate. The cholesteryl sulphate controls the proliferation and desquamation of keratinocytes and controls water balance. The increase of cholesteryl sulphate concentration also stimulates the hydration of the corneocytes-intercellular matrix boundary, increases desquamation of corneocytes and permeability of the stratum corneum.

Cholesteryl esters are a natural component of biomembranes and cholesteryl esters found in cell membranes are enzymatically hydrolyzed into cholesterol and transported in the blood plasma of all animals, where the cholesterol is methanolically utilized by an organism. Cholesteryl esters are an essential structural component of mammalian cell membranes, which establish proper membrane permeability and fluidity. The establishment of proper membrane permeability and fluidity from the cholesteryl esters also is reversible. Cholesteryl esters generally do not cause allergic reactions and skin irritation. Moreover, cholesteryl esters generally intensify penetration of active compounds and act relatively fast after application. Delivery rate also peaks in 1-3 hours, which is relatively faster than other transdermal delivery systems.

FIG. 1 illustrates an exemplary formulation in accordance with an embodiment of the present invention. In this figure, R denotes the residuum of carbonic acid which is part of the cholesteryl ester.

Some preferred embodiments of the present invention provide means and methods for providing a transmembrane/transdermal penetration enhancer with various active ingredients to be transdermally delivered. An active ingredient is a drug for attempting prevention and treatment of various diseases and maintenance and improvement of health and beauty for mammals including human beings. In some embodiments a limitation factor for a transmembrane/transdermal delivery when using a penetration enhancer is that the molecular weight of the active ingredients is under 1000.

In a non-limiting example, the following active ingredients can be used for transmembrane/transdermal penetration:

Psychoactive drugs including, but not limited to, 1,4-benzodiazepines: diazepam, oxazepam, lorazepam, clonazepam, bromazepam, alprazolam, clotiazepam; 1,5-benzodiazepine: clobazam; buspirone; amphetamines and related compounds: amfetamine, metamfetamine, methylphenidate; anorectics: cathine, fenfluramine; nootropics: piracetam, meclofenoxate;

Hypnotics including, but not limited to, nitrazepam, flunitrazepam, triazolam, brotizolam, phenobarbital, pentobarbital, etc.;

Analeptics including, but not limited to, doxapram, etc.;

Analgesics including, but not limited to, morphine, hydromorphone, oxycodone, oxymorphone, levorphanol, levomethadone, butorphanol, tramadol, fentanil, acetylsalicylic acid, salicylic acid derivatives, indometacin, diclofenac, ibuprofen, etc.;

Local anesthetics including, but not limited to, benzocaine, lidocaine, procaine, etc.;

Muscle relaxants including, but not limited to, baclofen, memantine, tizandine, etc.;

Antiepileptics including, but not limited to, primidone, phenytoin, carbamazepine, etc.;

Antiparkinsonian drugs including, but not limited to, trihexyphenidyl, biperiden, selegiline, etc.;

Hormones including, but not limited to, corticosteroids: hydrocortisone, prednisone, fluocortolone, paramethasone, betamethasone, estradiol, progesterone, gestagens: norgestrel, levonorgestrel, norethindrone; androgens: testosterone, mesterolone, etc.;

Drugs for Cardiovascular system including, but not limited to, nitroglycerin, β-blockers, nifedipine, etc.;

Anti-virals including, but not limited to, acyclovir, remantadine, ganciclovir, zidovudine, etc.;

Immunomodulators including, but not limited to, cyclosporine, etc.; and

Vitamins including, but not limited to, vitamin K, vitamin E, vitamin A, vitamin D, etc.

Some preferred embodiments, and variations thereof, of the present invention provide a transmembrane/transdermal penetration enhancer that boosts and enhances penetrability of skin. Another aspect of the present invention is to provide delivery of active ingredients of a transmembrane/transdermal penetration enhancer through skin and avoiding skin hydrotation and increasing the rate and efficiency of transdermal delivery by delivering a maximum amount of the active ingredients to be used in the body.

An embodiment of the present invention provides a thermotropic liquid crystal as a penetration enhancer for biomembranes and non-damaged skin that includes one or a mixture of two or more cholesterol esters as a penetration enhancer for biomembranes and non-damaged skin. In another aspect of the present invention, the thermotropic liquid crystal can also exhibit properties of a penetration enhancer when in a mesomorphic state.

Example 1

An embodiment of the present invention provides a thermotropic liquid crystal penetration enhancer that can be prepared by mixing two or more cholesteryl esters according to the mass ratios described in Table 1. The ratios described result in the thermotropic liquid crystal having a mesamorphic state at skin temperature. Other ratios may be used if the resultant thermotropic liquid crystal exhibits mesomorphic state at skin or application temperature. The prepared thermotropic liquid crystal penetration enhancer can be fused (melted down), shuffled (mixed together) and left open at room temperature (at approximately 18° C.) and can also be preserved by refrigeration to better preserve the enhancer and any added active ingredient.

TABLE 1

| N° of Example | cholesteryl pelargonate | cholesteryl valerate | cholesteryl succinate | cholesteryl adipinate | cholesteryl nanilsuccinate | cholesteryl propionate |
|---|---|---|---|---|---|---|
| | | | Ingredients, mass % | | | |
| 3 | 45 | 25 | 30 | | | |
| 4 | 50 | 25 | | 25 | | |
| 5 | 52.9 | 21.4 | 25.7 | | | |
| 6 | 85 | | | | | 15 |
| 7 | 47 | 25 | | | 28 | |

Example 2

Another embodiment of the present invention provides a method for preparing a base for a transmembrane/transdermal penetration enhancer that includes mixing two or more cholesterol esters according to a multiplicity of mass ratios described in Table 1. The prepared thermotropic liquid crystal penetration enhancer can be fused, shuffled and left open at room temperature (at approximately 18° C.) and can also be preserved by refrigeration. In a non-limiting example, the transmembrane/transdermal penetration enhancer is a solid lipophilic matrix that is approximately 1 cm.×1 cm.×0.1 cm in volume with a mass of less than 50 mg. At skin or application temperatures the enhancer is in a mesamorphic state.

Example 3-7

Other embodiments of the present invention provide a multiplicity of compositions for a transmembrane/transdermal penetration enhancer for biomembranes and skin with different mass ratios of active ingredients are outlined in Table 1.

Example 8-17

Other embodiments of the present invention provide a multiplicity of compositions for a base for a transmembrane/transdermal penetration enhancer with a multiplicity of different ratios of active ingredients. A non-limiting example of combinations are described in Table 2. Ratios of active ingredients are generally determined by the desired therapeutic dose to deliver.

Example 18

A non-limiting example of another embodiment of the present invention provides a composition of a base of a transmembrane/transdermal penetration enhancer that includes 49.9 mg of n-oxybenzal-n-butylaniline and n-metoxybenzal-n-butylaniline and an active ingredient of 0.1 mg of diazepam.

Example 19

A non-limiting example of another embodiment of the present invention provides a base of a transmembrane/transdermal penetration enhancer that includes 49.9 mg of 4-cyano-4-amyldiphenyl and an active ingredient of 0.1 mg of clonazepam.

Example 20

In support of another embodiment of the present invention, a supporting experiment was conducted where the backs of 55 white male mice were shaven, and the shaven backs were washed with lukewarm water and 50 mg of the multiplicity of mass ratios for a base of a transmembrane/transdermal penetration enhancer according to Examples 8-17 which were applied to approximately 1.0 cm$^2$ of the shaven area. Benchmark transdermal delivery systems (TDS) were used to compare invention with existing transdermal penetration enhancers. TDS include polyvinyl alcohol and 1,2-propylene glycol. 1,2-propylene glycol and lauric acid are prior art penetration enhancers. After two hours from the time of the application, an anticonvulsant action of the administered diazepam and clonazepam was measured by antagonism by intravenous administration of

TABLE 2

| Ingredients of base | | N° of example | | | | | | | | | |
|---|---|---|---|---|---|---|---|---|---|---|---|
| | | 8 | 9 | 10 | 11 | 12 | 13 | 14 | 15 | 16 | 17 |
| Cholesteryl pelargonate | Ingredients, mass % | 45 | 48.8 | 52.8 | 84.8 | 47 | 45 | 48.8 | 52.8 | 84.8 | 47 |
| Cholesteryl valerate | | 25 | 25 | 21.3 | | 25 | 25 | 25 | 21.3 | | 25 |
| Cholesteryl succinate | | 29.8 | | 25.7 | | | 29.8 | | 25.7 | | |
| Cholesteryl adipinate | | | 25 | | | | | 25 | | | |
| Cholesteryl nanilsuccinate | | | | | | 27.8 | | | | | 27.8 |
| Cholesteryl propionate | | | | | 15 | | | | | 15 | |
| Diazepam | | 0.2 | 0.2 | 0.2 | 0.2 | 0.2 | | | | | |
| Clonazepam | | | | | | | 0.2 | 0.2 | 0.2 | 0.2 | 0.2 |

1% solution of the pentylentetrazole. The pharmacological actions were then measured in terms of changes of the minimal effective dose (MED) of pentylenetetrazole for inducing clonic-tonical convulsions (DCTC) and tonical extension (DTE), which are described in Table 3. Higher numbers in DCTC and DTE columns for rows 8-17, corresponding to examples 8-17 of Table 2, show improved higher efficiency of penetration enhancers according to the present invention.

TABLE 3

| Example | Pharmacology effect | |
|---|---|---|
| | DCTC (pentylentetrazole, mg/kg ) | DTE (pentylentetrazole, mg/kg) |
| Control | 121 ± 9 | 147 ± 8 |
| TDS + 0.4% clonazepam | 198 ± 11 | 205 ± 11 |
| TDS + 0.4% diazepam | 170 ± 8 | 185 ± 9 |
| TDS + 10% lauric acid + 0.4% clonazepam | 240 ± 11 | 258 ± 10 |
| TDS + 10% lauric acid + 0.4% diazepam | 216 ± 9 | 225 ± 8 |
| 8 | 300 ± 12 | 340 ± 13 |
| 9 | 320 ± 14 | 355 ± 14 |
| 10 | 280 ± 8 | 320 ± 9 |
| 11 | 240 ± 13 | 260 ± 13 |
| 12 | 260 ± 11 | 280 ± 12 |
| 13 | 380 ± 9 | 400 ± 18 |
| 14 | 430 ± 16 | 460 ± 17 |
| 15 | 330 ± 12 | 375 ± 14 |
| 16 | 327 ± 15 | 370 ± 16 |
| 17 | 380 ± 17 | 420 ± 13 |

Example 21

In support of another embodiment of the present invention, a supporting experiment provides a 1% solution of pentylenetetrazole administered into the tail vein of a multiplicity of mice with an administration speed of 0.01 ml/sec. This method is concentration dependent, quickly-reversible and defines the correct delivery of the active substances. The control group of mice has an application area of 1 cm² for the base of a transmembrane/transdermal penetration enhancer without any active substances. Results of the application showed that the diazepam and clonazepam increase minimal effective dose of pentylenetetrazole for inducing clonic-tonical convulsions (DCTC) and tonical extension (DTE) of the mice, as described in Table 3.

Example 22

In support of another embodiment of the present invention, a supporting experiment was conducted where the backs of 3 white male rats that weighed approximately 150 g. were shaved and the backs of the rats were shaved and washed with lukewarm water and approximately 25 cm² of the base of a transmembrane/transdermal penetration enhancer described in Example 14 was administered. The base contained 10 mg of clonazepam and after six hours from the time of the application, the rats were killed and blood, brain and skin were taken from the application area. The amount of clonazepam in the organs and tissues of the killed rats were identified by HPLC method.

The amount of clonazepam in 1 cm³ of blood was 0.043±0.002 mg., in 1 g of brain 0.016±0.001 mg, in 1 cm² of the skin at the application area—0.04±0.002 mg. Amount of penetrated/permeated clonazepam during 6 hours through 25 cm² application area was 60% of applied amount.

Example 23

Figure 2:
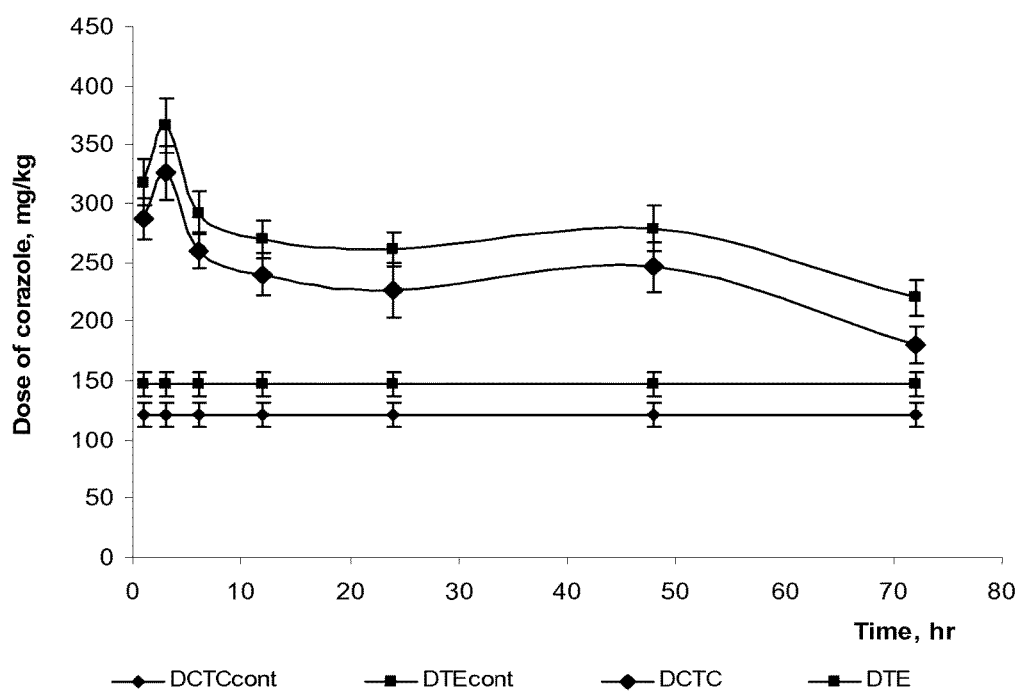
FIG. 2 illustrates an exemplary graph of the anticonvulsant action of diazepam after transdermal delivery in accordance with an embodiment of the present invention.

In support of another embodiment of the present invention, a supporting experiment was conducted where the backs of 40 white male mice were shaved, and the shaved portion was washed with lukewarm water and 50 mgs. of the base of a transmembrane/transdermal penetration enhancer according to Examples 9-17 was applied to an area of 1.0 cm² on the shaven portion of the mice. After 1 to 72 hours from the time of the application, the anticonvulsant action of the penetrated diazepam by antagonism with 1% solution of the pentylenetetrazole was identified. FIG. 2 illustrates an exemplary graph of the anticonvulsant action of diazepam after transdermal delivery in accordance with an embodiment of the present invention. The control group mice were administered 1 cm² of the transmembrane/transdermal penetration enhancer base without any active substances.

Example 24

Figure 3:
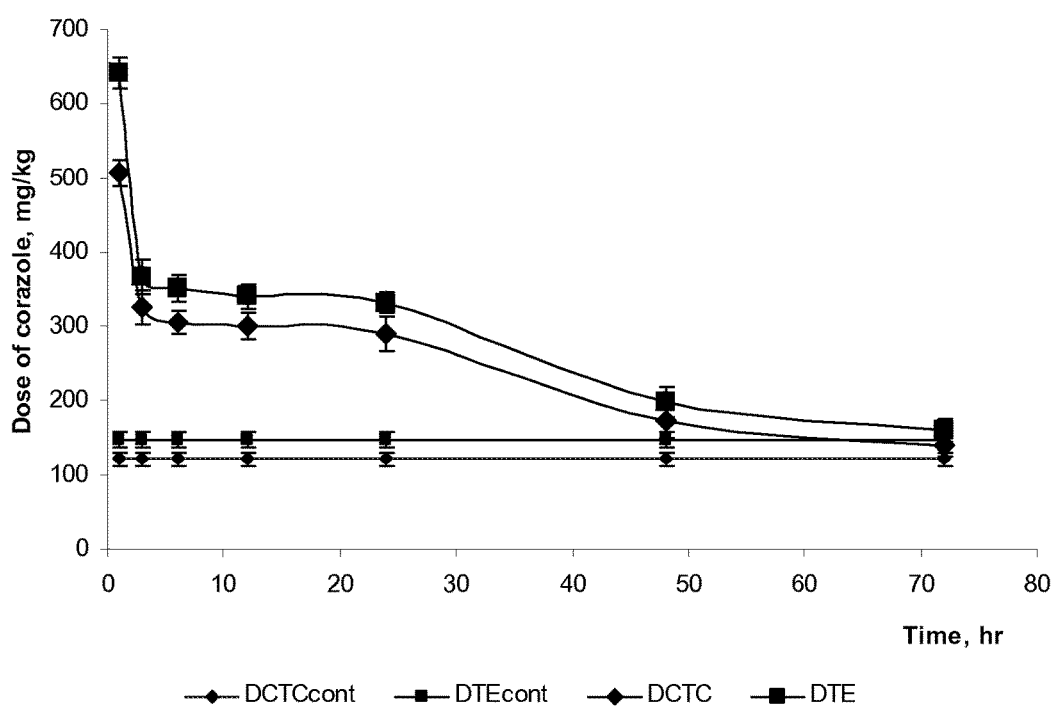
FIG. 3 illustrates an exemplary graph of the anticonvulsant action of clonazepam after transdermal delivery in accordance with an embodiment of the present invention.

In support of another embodiment of the present invention, a supporting experiment was conducted where the backs of 40 white male mice were shaved, and the shaved backs were washed with lukewarm water and 50 mg of the transmembrane/transdermal penetration enhancer base was applied to an area of 1.0 cm², according to Examples 9-17. After a period of time of 1 to 72 hours after the application, we identified the anticonvulsant action of the penetrated clonazepam by antagonism with 1% solution of the pentylenetetrazole. FIG. 3 illustrates an exemplary graph of the anticonvulsant action of clonazepam after transdermal delivery in accordance with an embodiment of the present invention. The transmembrane/transdermal penetration enhancer base was administered over a shaved area of 1 cm² to each white male mice of the control group without any active substances.

Example 25

In support of another embodiment of the present invention, a supporting experiment was conducted where the backs of 10 white male mice were shaved, and the shaved area was washed with lukewarm water and 50 mg of the transmembrane/transdermal penetration enhancer base applied to an area of 1.0 cm², that includes 49.9 mg of n-oxybenzal-n-butylaniline and n-metoxybenzal-n-butylaniline and 0.1 mg of diazepam, as previously described in Example 18. Two hours after the application, the anticonvulsant action of the penetrated diazepam and clonazepam by antagonism with 1% solution of the pentylenetetrazole was identified, as described in Table 4. The transmembrane/transdermal penetration enhancer base was administered over a shaved area of 1 cm² on the white male mice of the control group without any active substances.

Example 26

In support of another embodiment of the present invention, a supporting experiment was conducted where the backs of 10 white male mice were shaved and the shaved portion was washed with lukewarm water and 50 mg of a transmembrane/transdermal penetration enhancer base according to Example 19 was applied to an area of 1.0 cm². After two hours from the application, we identified the anticonvulsant action of the penetrated clonazepam by antagonism with 1% solution of the pentylenetetrazole, as is described in Table 4. The transmembrane/transdermal penetration enhancer base was administered over a shaved area of 1 cm² to each white male mice of the control group without any active substances.

TABLE 4

| | Pharmacology effect | |
|---|---|---|
| Example | DCTC (pentylenetetrazole, mg/kg) | DTE (pentylenetetrazole, mg/kg) |
| Control | 118 ± 7 | 147 ± 8 |
| 25 | 464 ± 16 | 492 ± 18 |
| 26 | 498 ± 17 | 516 ± 21 |

The experiment showed that the use of diazepam and clonazepam increases the minimal effective dose of pentylenetetrazole for inducing clonic-tonical convulsions (DCTC) and tonical extension (DTE) in the white male mice. The experiment also shows penetration across the skin of the white mice with a thermotropic liquid crystal penetration enhancer as a penetration enhancer and base.

Example 27

In support of another embodiment of the present invention, a supporting experiment was conducted where 10 white male mice were used and administrated 25 mg of transmembrane/transdermal penetration enhancer according to Example 4, with approximately 0.1 mg of clonazepam administrated to a white male mice rectums. After ½ hours, we identified the anticonvulsant action of the penetrated clonazepam by antagonism with 1% solution of the pentylenetetrazole in Table 5, with 25 mg of transmembrane/transdermal penetration enhancer without any active substances were administered to the white male mouse control group.

TABLE 5

| | Pharmacology effect | |
|---|---|---|
| Example | DCTC (pentylenetetrazole, mg/kg) | DTE (pentylenetetrazole, mg/kg) |
| Control | 123 ± 8 | 146 ± 9 |
| 25 | 445 ± 16 | 471 ± 19 |

The clonazepam increases the minimal effective dose of pentylenetetrazole for inducing clonic-tonical convulsions (DCTC) and tonical extension (DTE) of the white mice, which illustrate penetration across the mucous of the rectum by use of a thermotropic liquid crystal penetration enhancer.

In one embodiment a transmembrane penetration enhancer includes a thermotropic liquid crystal suitably prepared for use in a therapeutic system to improve delivery of at least one active ingredient through a biomembrane and/or skin. In another embodiment the thermotropic liquid crystal comprises at least one cholesteryl ester. In yet another embodiment the thermotropic liquid crystal exhibits a mesomorphic state at a temperature of the biomembrane and/or skin. Various other embodiments further include cholesteryl succinate, cholesteryl nanilsuccinate, or cholesteryl adipinate. By way of example, in still other embodiments the thermotropic liquid crystal comprises a mixture of cholesteryl pelargonate and cholesteryl valerate are combined with a third ingredient selected from the following: cholesteryl succinate, cholesteryl nanilsuccinate, or cholesteryl adipinate. Other embodiments comprise the following triple combinations: cholesteryl pelargonate, cholesteryl valerate and cholesteryl succinate; cholesteryl pelargonate, cholesteryl valerate and cholesteryl nanilsuccinate; or cholesteryl pelargonate, cholesteryl valerate and cholesteryl adipinate;

Those skilled in the art, in light of the foregoing teachings of the present invention will readily recognize a multiplicity of yet other suitable combinations to achieve a practical transmembrane and/or skin penetration enhancer depending upon the needs of the particular application.

Although various examples of the present invention for the transmembrane penetration enhancer were given above, it is anticipated that the transmembrane penetration enhancer can be used as part of suppositories for rectal and vaginal administration of drugs. It is further anticipated that the transmembrane penetration enhancer can be used as part of adhesive systems such as, but not limited to, films, patches, bandages, sprays for, but not limited to, rectal, vaginal, transdermal, and intranasal administration of drugs. It is also anticipated that the transmembrane penetration enhancer can be used as part of an ointment such as, but not limited to, gel or cream base for, but not limited to, rectal, vaginal, transdermal, intranasal and transbuccal administration of drugs. Furthermore the transmembrane penetration enhancer can be used as part of an ointment such as, but not limited to, a gel or cream base for ear disease. It is also anticipated that the transmembrane penetration enhancer can be used as part of liquid sprays for intranasal administration of drugs. The transmembrane/transdermal penetration enhancer can also be used with ultrasound for synergistic effect on transdermal drug delivery. The transmembrane/transdermal penetration enhancer can further be used with iontophoresis for synergistic effect on transdermal drug delivery. It is also anticipated that the transmembrane/transdermal penetration enhancer can be used with electroporation for synergistic effect on transdermal drug delivery. It is further anticipated that the transmembrane/transdermal penetration enhancer, in accordance with the present invention, can be used with various other physical methods, known to those skilled in the art, for drug delivery. In addition, it is also anticipated that the transmembrane/transdermal penetration enhancer, in accordance with the present invention, will be used with various other physical methods yet to be developed.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Having fully described at least one embodiment of the present invention, other equivalent or alternative methods for providing a transmembrane and transdermal penetration enhancer by which various active ingredients are transmenbrane and transdermally delivered, according to the present invention will be apparent to those skilled in the art. The invention has been described above by way of illustration, and the specific embodiments disclosed are not intended to limit the invention to the particular forms disclosed. For example, the particular implementation of the means and methods for providing a transmembrane and transdermal penetration enhancer by which various active ingredients are transmenbrane and transdermally delivered may vary depending upon the particular type used. The described in the foregoing were directed to implementations; however, similar techniques are implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A method for delivering an active agent through the skin of a patient in need thereof, said method comprising contacting the skin of said patient with a transmembrane penetration enhancer consisting of said active agent, wherein said transmembrane penetration enhancer is a thermotropic liquid crystal transmembrane penetration enhancer consisting of:
   1) one or a fused mixture of two or more cholesteryl esters in an amount of 90% or more; and
   2) an active agent selected from the group consisting of diazepam, oxazepam, lorazepam, clonazepam, bromazepam, alprazolam, clotiazepam, clobazam, buspirone, amphetamine, methamphetamine, methylphenidate, cathine, fenfluramine, piracetam, and meclofenoxate, in an amount of 10% or less;

wherein said thermotropic liquid crystal transmembrane penetration enhancer delivers said active agent through the skin of the patient when said cholesteryl esters are in a mesomorphic state.

2. The method as recited in claim 1, in which said one or more cholesteryl esters is selected from a group consisting of cholesteryl pelargonate, cholesteryl valerate, cholesteryl succinate, cholesteryl adipinate, cholesteryl nanilsuccinate and cholesteryl propionate.

3. The method as recited in claim 1, in which said combination is operable to improve transmembrane penetration.

4. The method as recited in claim 1, in which said combination is operable to improve transmucosal penetration.

* * * * *